(12) United States Patent
Backes et al.

(10) Patent No.: US 10,765,784 B2
(45) Date of Patent: Sep. 8, 2020

(54) CONTAINER FOR DRAINAGE OF FLUIDS OR WOUND SECRETION

(71) Applicant: PFM MEDICAL AG, Cologne (DE)

(72) Inventors: Daniel Backes, Gusenburg (DE); Christian Baumeister, Trier (DE); Nadine Kannwischer, Cologne (DE)

(73) Assignee: PFM MEDICAL AG, Cologne (DE)

( * ) Notice: Subject to any disclaimer, the term of this patent is extended or adjusted under 35 U.S.C. 154(b) by 245 days.

(21) Appl. No.: 15/406,061

(22) Filed: Jan. 13, 2017

(65) Prior Publication Data

US 2017/0203016 A1    Jul. 20, 2017

(30) Foreign Application Priority Data

Jan. 14, 2016 (DE) .................... 20 2016 100 153 U

(51) Int. Cl.
*A61M 1/00* (2006.01)
*A61M 39/28* (2006.01)

(52) U.S. Cl.
CPC ........ *A61M 1/0023* (2013.01); *A61M 1/0003* (2013.01); *A61M 1/008* (2013.01); *A61M 1/0021* (2013.01); *A61M 1/0033* (2014.02); *A61M 1/0035* (2014.02); *A61M 1/0052* (2014.02); *A61M 1/0074* (2013.01); *A61M 39/28* (2013.01); *A61M 2205/3379* (2013.01); *A61M 2205/583* (2013.01); *A61M 2205/7536* (2013.01)

(58) Field of Classification Search
CPC .............. A61M 1/0003; A61M 1/0023; A61M 1/0021; A61M 1/0052; A61M 1/0074; A61M 1/008; A61M 2205/7536; A61M 39/28

See application file for complete search history.

(56) References Cited

U.S. PATENT DOCUMENTS

| 3,334,628 A | * | 8/1967 | Saemann ............ A61M 1/0003 116/268 |
| 3,889,677 A |   | 6/1975 | Nehring |
| 4,402,687 A |   | 9/1983 | Denty et al. |

(Continued)

FOREIGN PATENT DOCUMENTS

| DE | 2454746 | 5/1975 |
| DE | 8530626 | 2/1986 |

(Continued)

*Primary Examiner* — Kai H Weng
(74) *Attorney, Agent, or Firm* — Grossman, Tucker, Perreault & Pfleger PLLC

(57) ABSTRACT

The invention relates to a container for drainage of fluids or wound secretion, comprising an inlet opening to connect with a drainage line and an outlet opening for releasing waste air accumulated inside the container during drainage, which is characterized in that the container is pre-evacuated, and the outlet opening is sealable, so that the container is transferable in a first and in a second operating condition, wherein in the first operating condition the outlet opening is sealed, so that a suction can be achieved at the inlet opening caused by the vacuum inside the container, and in the second operating condition the outlet opening is opened, so that air can enter the container through the outlet opening and neutralize the vacuum present inside the container.

13 Claims, 3 Drawing Sheets

(56) References Cited

U.S. PATENT DOCUMENTS

| | | | | |
|---|---|---|---|---|
| 5,078,704 A | * | 1/1992 | Wejnar | A61M 1/0003 |
| | | | | 141/236 |
| 6,056,731 A | | 5/2000 | Koetke et al. | |
| 6,261,276 B1 | | 7/2001 | Reitsma | |
| 7,153,294 B1 | | 12/2006 | Farrow | |
| 2004/0116902 A1 | | 6/2004 | Grossman et al. | |
| 2007/0027433 A1 | * | 2/2007 | Garcia | A61M 1/0003 |
| | | | | 604/319 |
| 2009/0012493 A1 | * | 1/2009 | Harig | A61M 1/0003 |
| | | | | 604/404 |
| 2014/0243707 A1 | * | 8/2014 | Kerr | A61B 10/00 |
| | | | | 600/573 |

FOREIGN PATENT DOCUMENTS

| | | |
|---|---|---|
| DE | 8604614 | 4/1986 |
| DE | 4402687 | 8/1994 |
| DE | 19723197 | 12/1998 |

\* cited by examiner

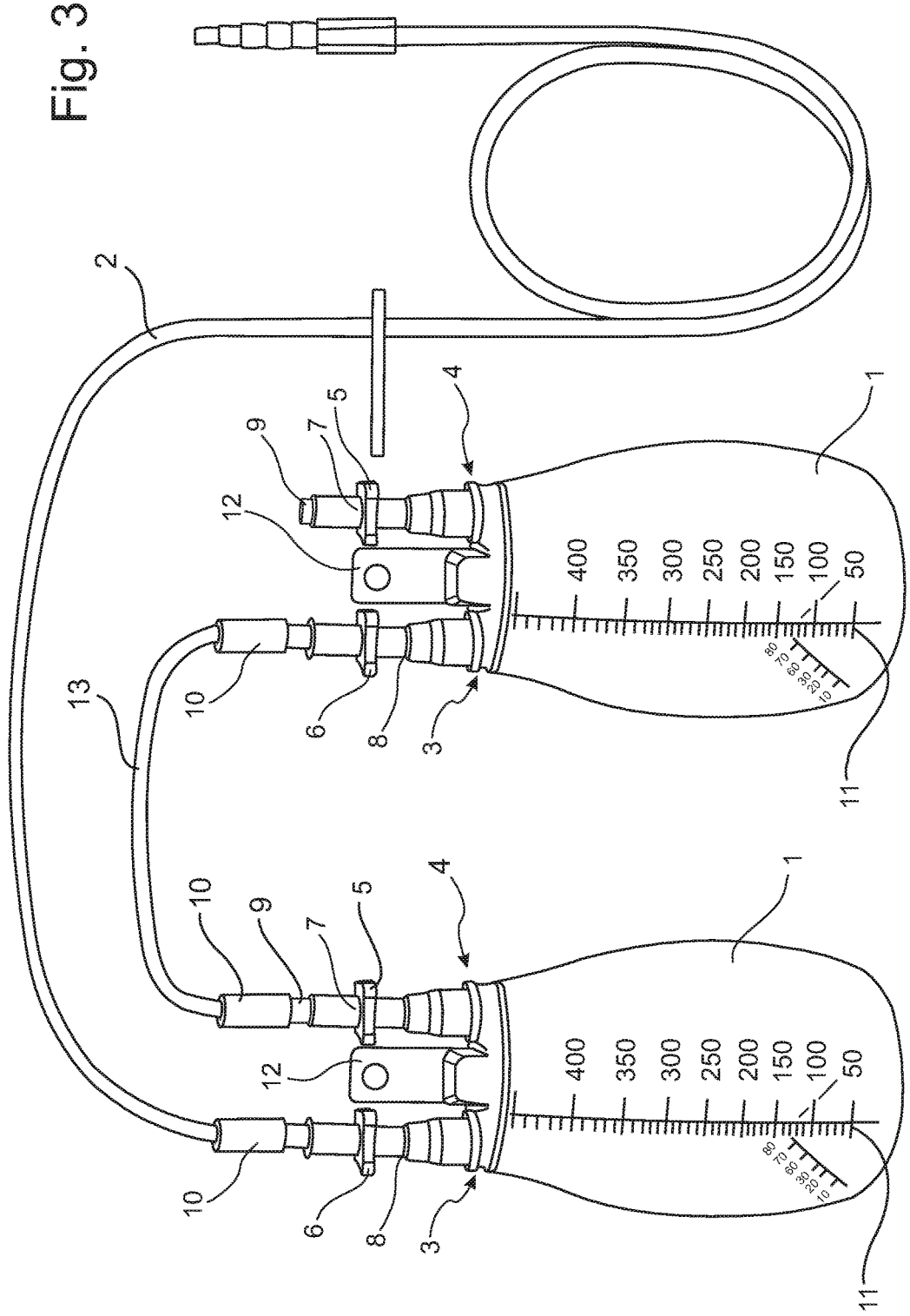

CONTAINER FOR DRAINAGE OF FLUIDS OR WOUND SECRETION

FIELD OF THE INVENTION

The invention relates to a container for drainage of fluids or wound secretion, comprising an inlet opening to connect with a drainage line and an outlet opening for releasing waste air accumulated inside the container during drainage.

BACKGROUND

From the prior art in principle two kinds of drainage are known for drainage of accumulated fluid or wound secretion.

According to a variant known from the prior art suction is created for drainage, so that fluid or wound secretion is aspirated. Therefore systems exist using a so-called high-vacuum or systems using a so-called low-vacuum. To create the suction a vacuum container is used, which is for example evacuated using a pump, so that inside the container is a vacuum. A drainage line is connectable to an opening of the vacuum container, wherein the distal end of the drainage line is connected to a body and/or tissue opening of the human or animal body, so that accumulated fluid can be aspirated.

Further, drainages for fluids or wound secretion are known, that function according to the principle of the so-called gravity drainage. No suction is used by these drainages to aspirate accumulated fluids or wound secretion, but the amount of fluid or wound secretion is accumulated in a container that passively collectable without creating a suction. The disadvantage of gravity drainages is that the initiation of the drainage is sometimes difficult because often no fluid or wound secretion actively exists the body and/or tissue opening of the human or animal body. However, situations exist, where gravity drainage is necessary, for example if a particularly gentle drainage is preferred at the body and/or tissue opening of the human or animal body or at the wound.

Starting from this prior art it is an object of the present invention to provide a container for drainage of fluids or wound secretion, which combines the advantages from the different kinds of drainage of fluids or wound secretion known from the prior art, so that a drainage using a vacuum (high- and/or low-vacuum drainage) and gravity drainage is possible using only one container.

SUMMARY

For technically solving this object according to the invention a container for drainage of fluids or wound secretion is proposed, comprising an inlet opening to connect with a drainage line and an outlet opening for releasing waste air accumulated inside the container during drainage, which is characterized in that the container is pre-evacuated and the outlet opening is sealable, so that the container is transferable in a first and in a second operating condition, wherein in the first operating condition the outlet opening is sealed, so that a suction can be achieved at the inlet opening caused by the vacuum inside the container, and in the second operating condition the outlet opening is opened, so that air can enter the container through the outlet opening and neutralize the vacuum present inside the container.

The invention bases on the findings that the advantages provided by a drainage according to a high-vacuum and/or low-vacuum drainage and provided by gravity drainage can be combined in one container. The usage of only one container for drainage of fluids is highly hygienic because aspirated or collected fluids or wound secretions are directly transferred through the drainage line into the inventive container.

The container according to the invention provides an operation in the first operating condition, according to which a suction at the inlet opening of the container is created by the vacuum inside the container, so that fluids or wound secretion can be aspirated according to a high-vacuum and/or low-vacuum drainage, and particularly provide a secure initiation of the drainage. During operation in the second operating condition, in which a vacuum inside the container is neutralized, so that no vacuum is present in the container or reservoir of the container, the drainage of wounds or post operation wounds, particularly at body and/or tissue openings of the human or animal body, is particularly gentle.

The invention allows that the kind of drainage can be changes during the drainage. The drainage can be started according to a vacuum drainage and afterwards be continued as gravity drainage. Thus, the drainage using the inventive container is particularly secure and drainage according to high-vacuum and/or low-vacuum drainage and as gravity drainage are possible using only one container, so that for example a change of the used systems during use with a patient to change the kind of drainage is no longer necessary. Particularly the complications for the patient associated with changing the drainage system can be avoided. Particularly the risk of contamination with microorganisms, which can result in infections of the wound or body opening of the patient to be aspirated or drained, is reduced by the solution according to the invention. The risk of contamination not only exists for the patient but also for the user, particularly the nursing staff or other third persons, which come into contact with the drainage. Furthermore, the risk of an unwanted loss of vacuum due to application or handling errors is reduced due to the intuitive solution according to the invention.

A preferred embodiment of the invention provides that outlet opening comprises a first tube-like element, wherein the first tube-like element of the outlet opening can be clamped or pinched off, so that the outlet opening is sealable. The first tube-like element is preferably directly connected with the outlet opening. If the first tube-like element is clamped or pinched off, no air, fluid or such the like can pass the first tube-like element, so that as a result the outlet opening of the container is closed airtight or vacuum tight.

In a further embodiment of the invention the first tube-like element of the outlet opening has a first clamping device, preferably a so-called slide-clamp, which can seal the outlet opening. Using the first clamping device the outlet opening of the first tube-like element of the outlet opening of the container can be clamped or pinched off, so that the outlet opening of the container is sealable. A slide-clamp has a recess tapered in a longitudinal direction, wherein the recess is tapered at one end in such a way, that a tube or tube-like element or such the like located inside the recess is clamped or pinched off. The opposing end of the recess is widened in such a way, that a tube or tube-like element, according to the invention the first tube-like element, located inside the recess is not clamped or pinched off.

A preferred embodiment of the invention is characterized in that the outlet opening comprises a filter, wherein the filter can act like a vent for releasing waste air from the container and entering air into the container. Thereby air enters via the filter and through the outlet opening into the container if the container is in the first operating condition and afterwards transferred into the second operating condition by opening the outlet opening, so that air entering the container can neutralize the vacuum present inside the container. In the second operating condition the vacuum inside the container is already neutralized or no vacuum is present inside the container, so that waste air inside the container, which for example enters into the container over the inlet opening during the drainage of fluids or wound secretion, can exit the container via the outlet opening, preferably via the filter of the outlet opening. The outlet opening of the container is thus opened, preferably by not clamping or pinching of the tube-like element. Preferably the filter is designed as a check valve. Preferably the valve is permeable for gasses, particularly air, and impermeable for liquids.

A preferred embodiment of the invention provides that the inlet opening is sealable. If the inlet opening as well as the outlet opening of the container is closed, the container is airtight or vacuum tight. Neither air can enter the container nor can air or fluid and/or wound secretion exist from the container. This allows a particular hygienic and secure disposal of the used container by the user.

In a further embodiment of the invention the inlet opening comprises a second tube-like element, wherein the second tube-like element of the inlet opening can be clamped or pinched off, so that the inlet opening is sealable. The second tube-like element is preferably directly connected with the inlet opening. If the second tube-like element is clamped or pinched off no air, liquid or such the like can pass the second tube-like element, so that as a result the inlet opening of the container is closed airtight or vacuum tight.

A preferred embodiment of the invention is characterized in that the second tube-like element of the inlet opening has a second clamping device, preferably a so-called slide-clamp, which can seal the inlet opening. The slide-clamp can be built like the previously described slide-clamp, so that the second tube-like element according to the invention arranged in the recess can be clamped or pinched off.

In a further embodiment of the invention the container is characterized in that the container has a capacity of about 400 ml to about 3000 ml, particularly preferred a capacity of about 1500 ml. Furthermore, in a further embodiment of the invention the total capacity is about 300 ml by connecting two containers with a capacity of about 1500 ml each, for example by connecting the two containers using a tube-like connecting element. This can be realized by connecting a tube-like element between the outlet opening of the first container and the inlet opening of the second container. A drainage line is connected to the inlet opening of the first container for drainage of fluids or wound secretion, and the outlet opening of the second container is sealable according to the invention, to provide an inventive first and second operating condition. Further, in an alternative embodiment both inlet openings of the two containers, with a capacity of about 1500 ml each, are connected to T-shaped connector, wherein the third connection of the T-shaped connector is connectable to a drainage line. The two outlet openings are each sealable to provide the inventive first and second operating condition.

If two or more containers are used, the single containers can be connected to each other by a supporting element. Thus, using the supporting element all containers could be handled at the same time. The supporting element preferably provides means for connecting a given amount of containers to the supporting element, like e.g. a specific number of hooks or holes for hooks. Furthermore, the containers could be connected to the supporting element by snap-fit connections. The supporting element can be further provided with mounting means for mounting the supporting element to a stand, particularly to an IV-stand or such the like. In a preferred embodiment the supporting is rigid and particularly is made of plastics.

In a preferred embodiment of the invention the container is pre-evacuated with about 40000 Pascal [Pa] to about 98000 Pascal [Pa]. A pre-evacuation of the container with about 40000 Pascal [Pa], which corresponds to about 400 mbar, enables a so-called low-vacuum drainage. A pre-evacuation of the container with about 98000 Pascal [Pa], which corresponds to about 980 mbar, enables a so-called high-vacuum drainage. However, also values between are possible, if these are necessary due to the particular circumstances. Thus, preferably a pre-evacuation between 0 Pascal [Pa] to about 100000 Pascal [Pa] is possible according to the invention.

In an embodiment of the invention the container has a scale, so that a user can see the filling level of the container. Further, the container is in a preferred embodiment designed as a so-called Redon-bottle or a so-called ASEPT-bottle. Advantageously the inventive container is a so-called Redon-bottle. A Redon-bottle consist of a rigid plastic and has compared to the prior art gravity drainage using plastic bags the advantage, that compared to the plastic bag the risk of damages caused by falling down, impacts, contact with sharp or pointed objects or such the like, is minimized.

A further embodiment of the invention provides that the container has no vacuum indicator despite the pre-evacuation, since due to the used material of the vacuum indicator air can permeate into the container. This would result in a reduced durability of the vacuum created during the manufacturing of the inventive container. The inlet opening of the container can comprise a so-called and standardized Luer-lock connector for an easy connection with a drainage line or drainage tube.

An exemplary use of the inventive container provides that the inlet opening and the outlet opening of the container are closed in the delivery condition, wherein the container is pre-evacuated. If the inlet opening of the container is opened by operating the second clamping device at the second tube-like element, at first a vacuum drainage—a low-vacuum or high-vacuum drainage depending on the pre-evacuation—is initiated, for example until the container is filled up to about 40% with aspirated fluid or wound secretion. Afterwards the outlet opening of the container is opened by operating the first clamping device at the first tube-like element, so that the vacuum inside the container is neutralized and the drainage is continued by gravity. In such a way the disadvantage of a pure gravity drainage with a difficult initiation of the drainage can be avoided because the drainage is started using the vacuum and afterwards a gentle drainage is performed using gravity.

In a second exemplary use the inlet opening and outlet opening are closed in the delivery condition, wherein the container is pre-evacuated. First the outlet opening is opened by operating the first clamping device at the first tube-like element. The vacuum present inside the container is neutralized by air entering through the outlet opening, so that the drainage with the inventive container is directly initiated and accomplished by gravity.

Further details, features and advantages of the invention will be explained in the following with respect to the embodiments shown in the figures.

BRIEF DESCRIPTION OF THE DRAWINGS

FIG. 3 is a schematic view of a further embodiment with two inventive containers with a drainage line for drainage of fluids or wound secretion in a side view.

DETAILED DESCRIPTION

Figure 1:
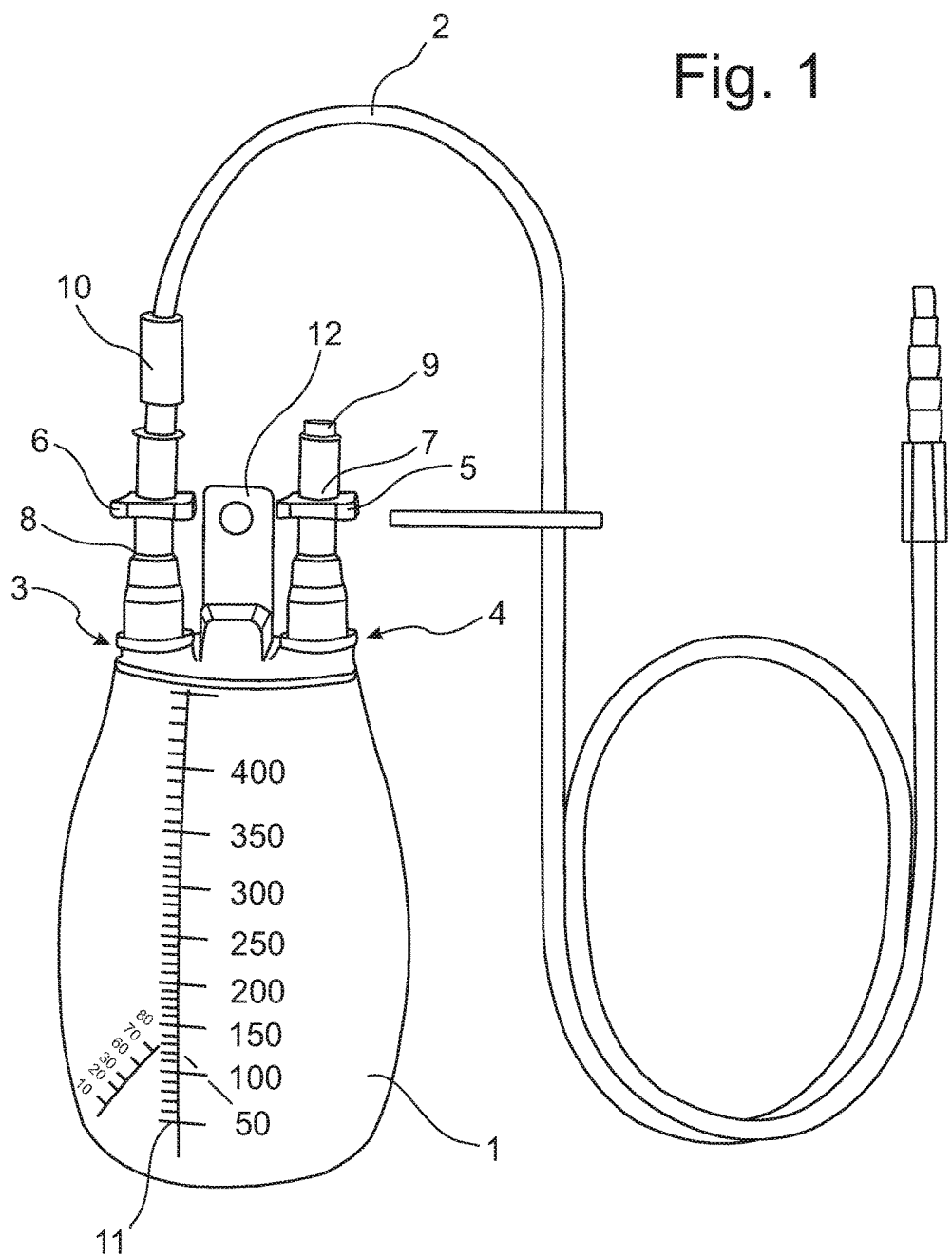
FIG. 1 is a schematic view of an embodiment of the inventive container with a drainage line for drainage of fluids or wound secretion in a side view.

FIG. 1 shows a container 1 in an embodiment of the invention for drainage of fluids or wound secretion in a schematic side view. The container 1 has an inlet opening 3, wherein the inlet opening 3 is connected with a drainage line 2 or a drainage tube 2. Further the container 1 has an outlet opening 4 for releasing waste air accumulated inside the container 1 during drainage. During manufacturing the container 1 has been pre-evacuated, presently with about 40000 Pascal [Pa], which corresponds to about 400 mbar. The container 1 consists of a rigid and transparent plastic, so that the container 1 does not change is form during evacuation. Further, the present container 1 is designed as a so-called Redon-bottle.

Directly at the outlet opening 4 of the container 2 a first tube-like element 7 is located, wherein the first tube-like element 7 of the outlet opening is clampable by a first clamping device 5, presently a slide-clamp 5. Thereby the outlet opening 4 of the container 1 is sealable.

Further, directly at the inlet opening 3 of the container 1 a second tube-like element 8 is located, wherein the second tube-like element 8 of the inlet opening 3 is clampable by a second clamping device 6, presently a slide-clamp 6. Thus, the inlet opening 3 of the container 1 is sealable by the slide-clamp 6. The inlet opening 1 of the container 1 comprises a so-called and standardized Luer-Lock connector 10, by which a corresponding counter-part of the drainage line 2 is easily connectable to the container 1.

The inventive container 1 is transferable in a first and in a second operating condition, wherein in the first operating condition the outlet opening 4 is closed, presently by pressing and adjusting the slide-clamp 5. If the inlet opening 3 is open, suction is generated at the inlet opening 3 due to the vacuum in the container 1 resulting from the pre-evacuation of the container 1. Via drainage line 2 located at the inlet opening 3, which in turn is connected to the not shown body and/or tissue opening of the human or animal body, fluid or wound secretion or such the like can be transferred by aspiration into the container 1.

If the outlet opening 4 of the container is opened, the container is transferred into a second operating condition, wherein via the opened outlet opening 4 air can enter the container 1, so that the vacuum inside the container 1 is neutralized. After no vacuum is present inside the container 1, the drainage functions according to the gravity drainage principle, which is a particular gentle drainage.

Further, the outlet opening 4 comprises a filter 9, wherein using the filter 9, as a kind of valve, waste air can be released from the container 1 or enter the container 1. The filter 9 can be for example designed that pressure differences between the inside of the container 1 and the air surrounding the container 1 are compensated. Further, the filter 9 is preferably designed that the filter 9 is permeable for gas, particular air, and impermeable for liquids, like for example wound secretion.

The container also has a scale 11, from which the user can identify the actual filling capacity of the container 1. Using a holder 12 the inventive container 1 can be mounted to a stand, IV-stand or such the like device.

Figure 2:
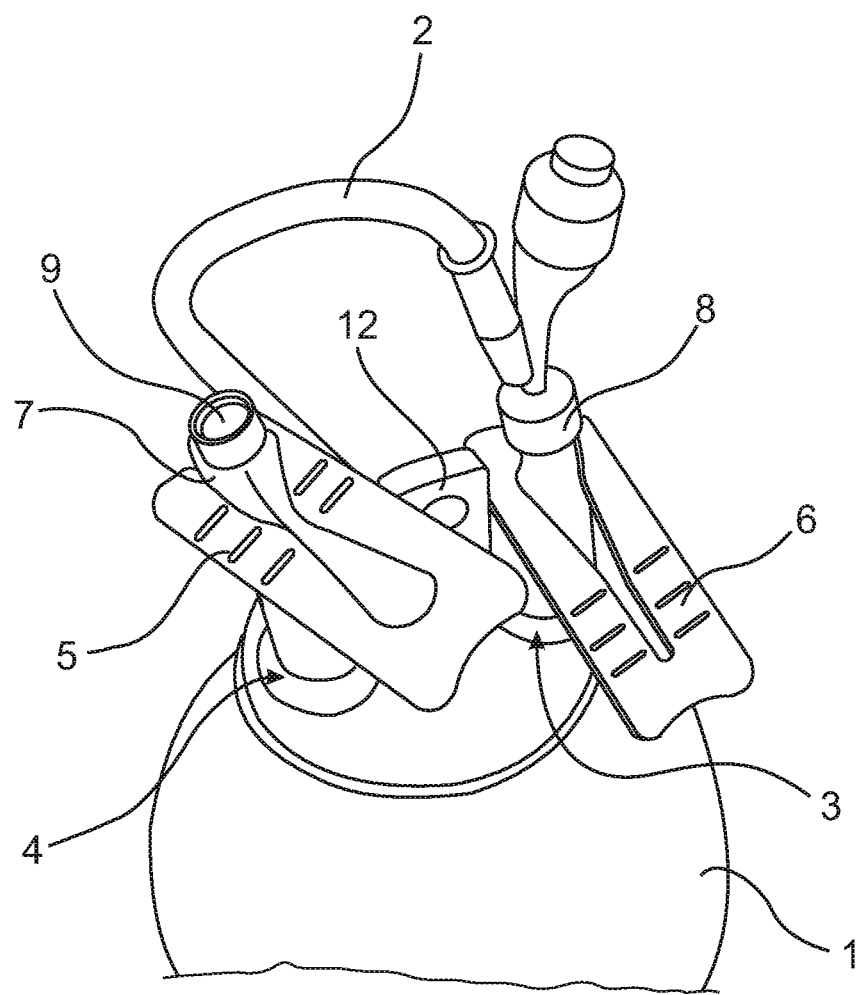
FIG. 2 is a schematic view of the embodiment of the inventive container according to FIG. 1 in a perspective top view.

FIG. 2 shows a schematic view of the embodiment of the inventive container 1 according to FIG. 1 in a perspective top view. The container 1 is presently in the first operating condition, in which the outlet opening 4 is sealed. This is accomplished by the slide-clamp 5. The slide-clamp 5 comprises a recess tapered in a longitudinal direction, wherein the recess is tapered at one end in such a way, that the tube-like element 7 of the outlet opening 4 located inside the recess is clamped or pinched off. The opposing end of the recess however is wide enough, that the tube-like element 7 of the outlet opening 7 arranged inside the recess is not clamped or pinched off.

A further slide-clamp 6 is arranged at the second tube-like element 8 of the inlet opening 3 of the container 1. In contrast to the slide-clamp 5 the second tube-like element 8 arranged inside the recess is in the widened part of the recess, so that the second tube-like element 8 is not clamped and therefore the inlet opening 3 of the container 1 is open. Suction is created at the inlet opening 3 by the vacuum inside the container 1, so that presently the first operating condition is adjusted and a vacuum-drainage is performed.

In FIG. 3 a further embodiment of a system for drainage of fluids or wound secretion is shown, which comprises two containers 1. The inventive containers 1 are connected to each other via a tube like connection piece or connecting line 13. A connection between the outlet opening 4 of the shown left container 1 is created to the inlet opening 3 of the shown right container 1. For easy handling by a user, as presently shown, the inlet or outlet openings 3 and 4 of the containers 1 each have Luer-Lock connectors 10.

Due to the shown embodiment it is possible to enhance the capacity to about 3000 ml. Further, it is possible that the capacity to further enhance the capacity by a sequence of inventive containers 1 connected in the same way, for example by a sequence of three or more containers 1 wherein connections between inlet openings 3 and outlet openings 4 are created.

The shown and described embodiments of the figures are only illustrative for the invention and are not limiting for the invention.

LIST OF NUMERALS 1 container (pre-evacuated)
2 drainage line
3 inlet opening
4 outlet opening
5 first clamping device (slide-clamp, outlet opening)
6 second clamping device (slide-clamp, inlet opening)
7 first tube-like element (outlet opening)
8 second tube-like element (inlet opening)
9 filter
10 Luer-lock connector
11 scale
12 holder
13 connecting line

What is claimed is:

1. A container for drainage of fluid and/or wound secretion, comprising:
   an inlet opening to connect with a drainage line, and
   an outlet opening to release waste air accumulated inside the container during drainage,
   wherein the container is pre-evacuated, and is rigid as not to change form when pre-evacuated,
   wherein the outlet opening is sealable, such that the container is transferable in a first operating condition and in a second operating condition, wherein, in the first operating condition, the outlet opening is sealed, such that a suction is achievable at the inlet opening by a vacuum inside the container, and wherein, in the second operating condition, the outlet opening is opened, such that air is enterable into the container through the outlet opening which neutralizes the vacuum inside the container, whereby drainage of fluid and/or wound secretion is startable according to a vacuum drainage and afterwards is continuable as gravity drainage, wherein the outlet opening comprises a first tubular element, which is at least one of clampable or pinchable to seal the outlet opening, wherein the outlet opening comprises a filter, which is configured to provide a vent which is operable for at least one of air to release from the container or for air to enter into the container, wherein the filter is gas permeable and liquid impermeable; and wherein the container is pre-evacuated in a range of 40,000 Pascal to 98,000 Pascal.

2. The container according to claim 1, wherein the first tubular element is clampable or pinchable by a clamping device to seal the outlet opening.

3. The container according to claim 2, wherein the clamping device comprises a slide-clamp.

4. The container according to claim 1, wherein the filter is permeable to air and impermeable to the drainage fluid and/or the wound secretion.

5. The container according to claim 1, wherein the inlet opening is sealable.

6. The container according to claim 1, wherein the inlet opening comprises a second tubular element, wherein the second tubular element is at least one of clampable or pinchable to seal the inlet opening.

7. The container according to claim 6, wherein the second tubular element of the inlet opening is clampable or pinchable by a clamping device to seal the inlet opening.

8. The container according to claim 7, wherein the clamping device comprises a slide-clamp.

9. The container according to claim 1, wherein the container has a capacity in a range of about 400 ml to about 3000 ml.

10. The container according to claim 1, wherein the container comprises a bottle and a bottle cap.

11. The container according to claim 1, wherein the container is formed of plastic.

12. The container according to claim 11, wherein the plastic is a transparent plastic.

13. The container according to claim 11, wherein the plastic is a rigid plastic.

* * * * *